United States Patent
Liddle

(10) Patent No.: US 9,452,169 B2
(45) Date of Patent: Sep. 27, 2016

(54) SUBSTITUTED DIKETOPIPERAZINES AND THEIR USE AS OXYTOCIN ANTAGONISTS

(71) Applicant: Glaxo Group Limited, Brentford, Middlesex (GB)

(72) Inventor: John Liddle, Stevenage (GB)

(73) Assignee: GLAXO GROUP LIMITED, Brentford, Middlesex (GB)

( * ) Notice: Subject to any disclaimer, the term of this patent is extended or adjusted under 35 U.S.C. 154(b) by 0 days.

(21) Appl. No.: 14/946,920

(22) Filed: Nov. 20, 2015

(65) Prior Publication Data

US 2016/0074413 A1 Mar. 17, 2016

Related U.S. Application Data

(63) Continuation of application No. 14/570,812, filed on Dec. 15, 2014, now abandoned, which is a continuation of application No. 14/072,376, filed on Nov. 5, 2013, now Pat. No. 8,937,179, which is a continuation of application No. 13/715,433, filed on Dec. 14, 2012, now abandoned, which is a continuation of application No. 13/231,211, filed on Sep. 13, 2011, now Pat. No. 8,357,685, which is a continuation of application No. 10/561,498, filed as application No. PCT/EP2004/006814 on Jun. 22, 2004, now Pat. No. 8,071,594.

(30) Foreign Application Priority Data

Jun. 24, 2003 (GB) .................................. 0314738.6

(51) Int. Cl.

| A61K 31/5377 | (2006.01) |
| C07D 413/06 | (2006.01) |
| C07D 413/14 | (2006.01) |
| C07D 241/08 | (2006.01) |
| A61K 9/00 | (2006.01) |

(52) U.S. Cl.
CPC ......... *A61K 31/5377* (2013.01); *A61K 9/0053* (2013.01); *C07D 241/08* (2013.01); *C07D 413/06* (2013.01); *C07D 413/14* (2013.01)

(58) Field of Classification Search
USPC ...................................... 514/255.05; 544/366
See application file for complete search history.

(56) References Cited

U.S. PATENT DOCUMENTS

| 4,596,819 | A | 6/1986 | Nicolaides et al. |
| 5,464,788 | A | 11/1995 | Bock et al. |
| 5,817,751 | A | 10/1998 | Szardenings et al. |
| 5,968,938 | A | 10/1999 | Williams et al. |
| 6,107,274 | A | 8/2000 | Mjalli et al. |
| 7,514,437 | B2 | 4/2009 | Borthwick et al. |
| 8,071,594 | B2* | 12/2011 | Liddle ................. C07D 413/06 514/235.5 |
| 8,357,685 | B2* | 1/2013 | Liddle ................. C07D 413/06 514/235.5 |
| 8,367,673 | B2 | 2/2013 | Borthwick et al. |
| 8,937,179 | B2* | 1/2015 | Liddle ................. C07D 413/06 544/366 |
| 2003/0229001 | A1 | 12/2003 | Naylor et al. |
| 2005/0148572 | A1 | 7/2005 | Borthwick et al. |
| 2007/0149524 | A1 | 6/2007 | Liddle |
| 2007/0185162 | A1* | 8/2007 | Borthwick ........... C07D 401/06 514/315 |
| 2007/0208031 | A1 | 9/2007 | Borthwick et al. |
| 2007/0254888 | A1 | 11/2007 | Borthwick et al. |
| 2014/0235556 | A1 | 8/2014 | Halse et al. |

FOREIGN PATENT DOCUMENTS

| GB | 2326639 | | 12/1998 |
| GB | 2372740 | | 9/2002 |
| WO | 9404513 | A1 | 3/1994 |
| WO | 9937304 | A1 | 7/1999 |
| WO | 9938844 | A1 | 8/1999 |
| WO | 9947549 | A1 | 9/1999 |
| WO | 03/053443 | * | 7/2003 |
| WO | 03053443 | A1 | 7/2003 |
| WO | 2005000311 | A1 | 1/2005 |
| WO | 2006000759 | A1 | 1/2006 |
| WO | 2006067462 | A1 | 6/2006 |

OTHER PUBLICATIONS

Akerlund et al.; Prog. Brain Res.; 2002; vol. 139; pp. 359-365; Abstract.
Banker et al.; Modern Pharmaceutics, 3rd Ed.; 1996; p. 596.
Testa et al.; Pure Appl. Chem.; 2004; vol. 76; pp. 907-914.
Tsataris et al.; Drugs; 2004; vol. 64, No. 4; pp. 375-382; Abstract.
Vippagunta et al.; Advanced Drug Delivery Reviews; 2001; vol. 48; pp. 3-26.
Wolff; Burger's Medicinal Chemistry, 5th Ed. Part 1; 1995; pp. 975-977.
Grigorash et al.; Chem. Heterocycl. Compound; 1977; vol. 13, No. 12; pp. 1280-1281.
Kolasa et al.; J. Org. Chem.; 1990; vol. 55, No. 6; pp. 1711-1721.
Pettibone et al.; Drug Development Research; 1993; vol. 30, No. 3; pp. 129-142.
Stella; Pro Drugs as Novel Drug Delivery Systems, Pro Drugs: An Overview and Definition; 1975; pp. 1-115.
Wyatt et al.; Bioorganic & Med. Chem. Letters; 2001; vol. 11, No. 10; pp. 1301-1305.
Sarnyai et al.; Psychoneuroendocrinology; 1994; vol. 19, No. 1; pp. 85-117.

\* cited by examiner

*Primary Examiner* — Sabiha N Qazi
(74) *Attorney, Agent, or Firm* — Jane F. Djung; Kathyrn A. Lutomski; Edward R. Gimmi

(57) ABSTRACT

Compounds of formula (1)

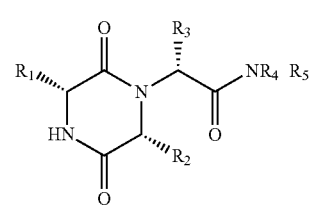

wherein $R_1$ is 2-indanyl, $R_2$ is 1-methylpropyl, $R_3$ is 2-methyl-1,3-oxazol-4-yl and $R_4$ and $R_5$ together with the nitrogen atom to which they are attached represents morpholino, process for their preparation, pharmaceutical compositions containing them and their use in medicine.

8 Claims, No Drawings

SUBSTITUTED DIKETOPIPERAZINES AND THEIR USE AS OXYTOCIN ANTAGONISTS

CROSS-REFERENCE TO RELATED APPLICATIONS

This application is a Continuation of U.S. patent application Ser. No. 14/570,812 filed Dec. 15, 2014, which is a Continuation of U.S. patent application Ser. No. 14/072,376 filed Nov. 5, 2013, issued as U.S. Pat. No. 8,937,179, which is a Continuation of U.S. patent application Ser. No. 13/715,433 filed Dec. 14, 2012, now abandoned; which is a Continuation of U.S. patent application Ser. No. 13/231,211 filed Sep. 13, 2011, issued as U.S. Pat. No. 8,357,685; which is a Continuation of U.S. patent application Ser. No. 10/561,498 filed Dec. 19, 2005, issued as U.S. Pat. No. 8,071,594; which was filed pursuant to 35 U.S.C. §371 as a U.S. National Phase Application of International Patent Application No. PCT/EP2004/006814 filed Jun. 22, 2004, which claims priority from Great Britain Application No. 0314738.6 filed Jun. 24, 2003.

FIELD OF THE INVENTION

This invention relates to novel diketopiperazine derivatives having a potent and selective antagonist action at the oxytocin receptor, to processes for their preparation, pharmaceutical compositions containing them and to their use in medicine.

BACKGROUND OF THE INVENTION

The hormone oxytocin is potent contractor of the uterus and is used for the induction or augmentation of labour. Also the density of uterine oxytocin receptors increases significantly by >100 fold during pregnancy and peaks in labour (pre-term and term).

Pre-term births/labour (between 24 and 37 weeks) causes about 60% of infant mortality/morbidity and thus a compound which inhibits the uterine actions of oxytocin e.g. oxytocin antagonists, should be useful for the prevention or control of pre-term labour.

International patent application PCT/EP02/14823 describes a class of diketopiperazine derivatives which exhibit a particularly useful level of activity as selective antagonists at the oxytocin receptor. A preferred class of compounds described therein is represented by the formula A

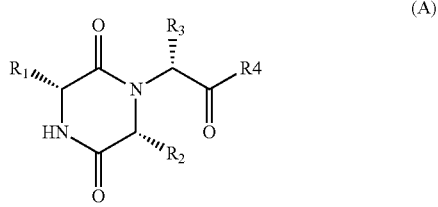

(A)

Such compounds include those wherein inter alia $R_1$ is 2-indanyl, $R_2$ is $C_{3-4}$alkyl, $R_3$ is a 5 or 6 membered heteroaryl group linked to the rest of the molecule via a carbon atom in the ring, $R_4$ represents the group $NR_5R_6$ wherein $R_5$ and $R_6$ each represent alkyl e.g. methyl or $R_5$ and $R_6$ together with the nitrogen atom to which they are attached form a 3 to 7 membered saturated heterocyclic ring which heterocycle may contain an additional heteroatom selected from oxygen.

DESCRIPTION OF THE INVENTION

We have now found a novel group of selective oxytocin receptor antagonists which exhibit a particularly advantageous pharmacokinetic profile.

The present invention thus provides compounds of formula (1)

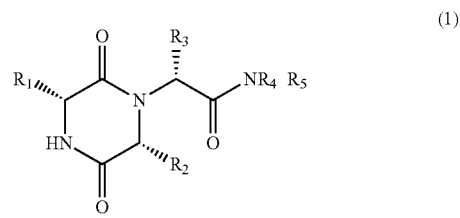

(1)

Wherein $R_1$ is 2-indanyl, $R_2$ is 1-methylpropyl, $R_3$ is 2-methyl-1,3-oxazol-4-yl and $R_4$ and $R_5$ together with the nitrogen atom to which they are attached represents morpholino.

The group $R_2$ contains an asymmetric carbon atom and the invention includes each enantiomer and mixtures thereof including the racemate.

A preferred compound of the invention is the compound the preparation of which is specifically described in example 1.

The compounds of formula (I) have a high affinity for the oxytocin receptors on the uterus of rats and humans and this may be determined using conventional procedure. For example the affinity for the oxytocin receptors on the rat uterus may be determined by the procedure of Pettibone et al, Drug Development Research 30. 129-142 (1993). The compounds of the invention also exhibit high affinity at the human recombinant oxytocin receptor in CHO cells and this may be conveniently demonstrated using the procedure described by Wyatt et al. Bioorganic & Medicinal Chemistry Letters, 2001 (11) p 1301-1305.

The compounds of the invention also exhibit an advantageous pharmacokinetic profile including good bioavailability and low intrinsic clearance when administered by i.v. or p.o. coupled with good stability to P450 enzymes including 2C9 and good aqueous solubility.

The compounds of the invention are therefore useful in the treatment or prevention of diseases and/or conditions mediated through the action of oxytocin. Examples of such diseases and/or conditions include pre-term labour, dysmenorrhea, endometriosis and benign prostatic hyperplasia.

The compounds may also be useful to delay labour prior to elective caesarean section or transfer of the patient to a tertiary care centre, treatment of sexual dysfunction, particularly premature ejaculation, obesity, eating disorders, congestive heart failure, arterial hypertension, liver cirrhosis, nephritic or ocular hypertension, obsessive-compulsive disorder and neuropsychiatric disorders. The compounds of the invention may also be useful for improving fertility rates in animals, e.g. farm animals.

The invention therefore provides for the use of a compound of formula (I) for use in therapy and in particular use as medicine for antagonising the effects of oxytocin upon the oxytocin receptor.

The invention also provides for the use of a compound of formula (I) for the manufacture of a medicament for antagonising the effects of oxytocin on the oxytocin receptor.

According to a further aspect, the invention also provides for a method for antagonising the effects of oxytocin upon the oxytocin receptor, comprising administering to a patient in need thereof an antagonistic amount of a compound of formula (I).

It will be appreciated by those skilled in the art that reference herein to treatment extends to prophylactics as well as the treatment of established diseases or symptoms.

It will further be appreciated that the amount of a compound of the invention required for use in treatment will vary with the nature of the condition being treated, the route of administration and the age and the condition of the patient and will be ultimately at the discretion of the attendant physician. In general however doses employed for adult human treatment will typically be in the range of 2 to 800 mg per day, dependent upon the route of administration.

Thus for parenteral administration a daily dose will typically be in the range 2 to 50 mg, preferably 5 to 25 mg per day. For oral administration a daily dose will typically be within the range 10 to 800 mg, e.g. 20 to 150 mg per day.

The desired dose may conveniently be presented in a single dose or as divided doses administered at appropriate intervals, for example as two, three, four or more sub-doses per day.

While it is possible that, for use in therapy, a compound of the invention may be administered as the raw chemical, it is preferable to present the active ingredient as a pharmaceutical formulation.

The invention thus further provides a pharmaceutical formulation comprising a compound of formula (I) together with one or more pharmaceutically acceptable carriers thereof and, optionally, other therapeutic and/or prophylactic ingredients. The carrier(s) must be 'acceptable' in the sense of being compatible with the other ingredients of the formulation and not deleterious to the recipient thereof.

The compositions of the invention include those in a form especially formulated for oral, buccal, parenteral, inhalation or insufflation, implant or rectal administration.

Tablets and capsules for oral administration may contain conventional excipients such as binding agents, for example, syrup, acacia, gelatin, sorbitol, tragacanth, mucilage of starch or polyvinylpyrrolidone; fillers, for example, lactose, sugar, microcystalline cellulose, maize-starch, calcium phosphate or sorbitol; lubricants, for example, magnesium stearate, stearic acid, talc, polyethylene glycol or silica; disintegrants, for example, potato starch or sodium starch glycollate, or wetting agents such as sodium lauryl sulphate. The tablets may be coated according to methods well known in the art. Oral liquid preparations may be in the form of, for example, aqueous or oily suspensions, solutions emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example, almond oil, fractionated coconut oil, oily esters, propylene glycol or ethyl alcohol; solubilizers such as surfactants for example polysorbates or other agents such as cyclodextrins; and preservatives, for example, methyl or propyl p-hydroxybenzoates or ascorbic acid. The compositions may also be formulated as suppositories, e.g. containing conventional suppository bases such as cocoa butter or other glycerides.

For buccal administration the composition may take the form of tablets or lozenges formulated in conventional manner.

The composition according to the invention may be formulated for parenteral administration by injection or continuous infusion. Formulations for injection may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for constitution with a suitable vehicle, e.g. sterile, pyrogen-free water, before use.

The compositions according to the invention may contain between 0.1-99% of the active ingredient, conveniently from 1-50% for tablets and capsules and 3-50% for liquid preparations.

The advantageous pharmacokinetic profile of the compounds of the invention is readily demonstrated using conventional procedures for measuring the pharmacokinetic properties of biologically active compounds.

Compounds of formula (1) may be prepared by reaction of the carboxylic acid (11, wherein $R_1$, $R_2$ and $R_3$ have the meanings defined in formula 1).

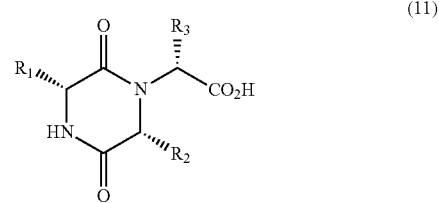

(11)

or an activated derivative thereof with the amine $NHR_4R_5$ wherein $NR_4R_5$ has the meaning defined in formula (1) under standard conditions for preparing amides from a carboxylic acid or a mixed anhydride thereof and an amine $HNR_4R_5$.

Thus the amide of formula (1) may be prepared by treating the carboxylic acid of formula (11) with an activating agent such as BOP (benzotriazol-1-yloxy-tris(dimethylamino)phosphonium hexafluorophosphate), TBTU (2-(1H-benzotriazol-1-yl)-1,1,3,3-tetramethyluronium tetrafluoroborate), BOP-Cl (bis(2-oxo-3-oxazolidinyl)phosphinic chloride) or oxalyl chloride in an aprotic solvent such as dichloromethane optionally in the presence of a tertiary amine such as triethylamine and subsequent reaction of the product thus formed with the amine $NHR_4R_5$.

Alternatively the amide of formula (1) may be prepared by reacting a mixed anhydride derived from the carboxylic acid (11) with the amine $NHR_4R_5$ in an aprotic solvent such as tetrahydrofuran. Conveniently the reaction is carried out at low temperatures e.g. approximately −78 C.

The mixed anhydride is conveniently prepared by reacting the carboxylic acid (11) with a suitable acid chloride e.g. pivavolyl chloride in an aprotic solvent such as ethyl acetate in the presence of a tertiary organic base such as a trialkylamine e.g. triethylamine and at low temperatures e.g. approximately −78 C.

Compounds of formula (1) may also be prepared by reacting a compound of formula (111)

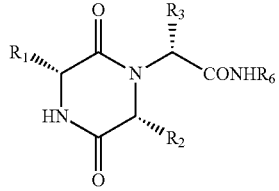
(111)

(wherein $R_1$, $R_2$ and $R_3$ have the meanings defined in formula (1) and $R_6$ is 2-hydroxy phenyl) with carbonyl diimidazole or thiocarbonyl diimidazole in a suitable solvent such as dichloromethane and subsequent reaction of the products this formed with the amine $HNR_4R_5$.

Compounds of formula (11) may be prepared from a compound of formula (111) wherein $R_6$ is 2-hydroxyphenyl by reaction with carbonyldiimidazole or thiocarbonyldiimidazole in a suitable solvent such as dichloromethane and subsequent reaction of the product thus formed with aqueous acetone.

Compounds of formula (111) wherein $R_6$ is 2-hydroxyphenyl may be from the corresponding compounds of formula (111) wherein $R_6$ is a 2-benzyloxyphenyl group by hydrogenolysis using hydrogen and a palladium catalyst.

Compounds of formula (111) wherein $R_6$ is a 2-benzyloxyphenyl group are conveniently prepared by the process described herein below.

Thus compounds of formula (III) may be prepared from the compound of formula (IV)

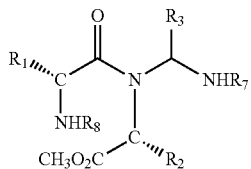
(IV)

wherein $R_1$, $R_2$ and $R_3$ have the meanings defined in formula (I), $R_7$ is 2-benzyloxyphenyl and $R_8$ is N-benzyloxycarbonyl by the reaction with hydrogen in the presence of a palladium on charcoal catalyst and acetic acid. This reaction is conveniently carried out in a solvent such as ethanol or trifluoroethanol or mixtures thereof.

The compound of formula (IV) may be prepared by reacting the amino ester hydrochloride (V), wherein $R_2$ has the meaning defined and formula (I)

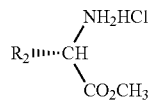
(VI)

with the aldehyde $R_3$CHO (VI) wherein $R_3$ has the meanings defined in formula (I), in the presence of triethylamine and in a solvent such as trifluoroethanol and then reacting of the resultant product with the compound (VII) wherein $R_1$ has the meanings defined in formula (I) and $R_7$ is a benzyloxycarbonyl

(VII)

and the isocyanide $CNR_6$ (VIII) wherein $R_6$ is a 2-benzyloxyphenyl group, in a solvent such as trifluoroethanol.

The $R_2$ substituent is a 1-methylpropyl group and the compound of formula (I) wherein $R_2$ is a 1-methylpropyl group having an (S) or (R) configuration may be prepared by starting with the aminoester (V) wherein the $R_2$ group has the required (S) or (R) configuration.

EXPERIMENTAL EXAMPLES

The following examples are illustrative, but not limiting of the embodiments of the present invention.

General Purification and Analytical Methods

Analytical HPLC was conducted on a Supelcosil LCABZ+PLUS column (3.3 cm×4.6 mm ID), eluting with 0.1% $HCO_2H$ and 0.01 M ammonium acetate in water (solvent A), and 0.05% $HCO_2H$ 5% water in acetonitrile (solvent B), using the following elution gradient 0-0.7 minutes 0% B, 0.7-4.2 minutes 0%-100% B, 4.2-5.3 minutes 100% B, 5.3-5.5 minutes 0% B at a flow rate of 3 ml/minute. The mass spectra (MS) were recorded on a Fisons VG Platform spectrometer using electrospray positive [(ES+ve to give $MH^+$ and $M(NH_4)^+$ molecular ions] or electrospray negative [(ES-ve to give $(M-H)^-$ molecular ion] modes on a Micromass series 2 or a Waters ZQ mass spectrometer. $^1H$ NMR spectra were recorded using a Bruker DPX 400 MHz spectrometer using tetramethylsilane as the external standard. Biotage™ chromatography refers to purification carried out using equipment sold by Dyax Corporation (either the Flash 40i or Flash 150i) and cartridges pre-packed with KPSil. Mass directed autoprep refers to methods where the material was purified by high performance liquid chromatography on a HPLCABZ+ 5 μm column (5 cm×10 mm i.d.) with 0.1% $HCO_2H$ in water and 95% MeCN, 5% water (0.5% $HCO_2H$) utilising gradient elution at a flow rate of 8 ml minutes$^{-1}$. The Gilson 202-fraction collector was triggered by a VG Platform Mass Spectrometer on detecting the mass of interest.

Hydrophobic frits refer to filtration tubes sold by Whatman. SPE (solid phase extraction) refers to the use of cartridges sold by International Sorbent Technology Ltd. TLC (thin layer chromatography) refers to the use of TLC plates sold by Merck coated with silica gel 60 $F_{254}$. Oasis™ refers to Waters® Oasis™ HLB Extraction Cartridges, sold by Waters Corporation®.

Intermediate 1

2-{(3R,6R)-3-(2,3-dihydro-1H-inden-2-yl)-6-[(1S)-1-methylpropyl]-2,5-dioxo-1-piperazinyl}-N-(2-hydroxyphenyl)-2-(2-methyl-1,3-oxazol-4-yl)acetamide To a vigorously stirred solution of (D)-allo Isoleucine methyl ester hydrochloride (5.0 g) in dichloromethane (150 ml) was added a saturated sodium bicarbonate solution (150 ml). The resultant bi-layer was separated using a hydrophobic frit and the aqueous phase washed twice with dichloromethane (50 ml). The combined dichloromethane phase was diluted with methanol (200 ml) and (2R)-[(benzyloxycarbonyl)amino](2,3-dihydro-1H-inden-2-yl)ethanoic acid (14.64 g) added and the mixture vigorously stirred for 1 hr to effect solution. The solution was evaporated and the residue dissolved in a mixture of 1:1 trifluoroethanol/methanol (140 ml), and then 2-benzyloxyphenylisocyanide (9.43 g) was added followed by 2-methyl-4-formyloxazole (5.0 g) and the reaction stirred for 4 days at room temperature. The mixture was evaporated and the residue dissolved in ethanol (500 ml) and palladium on carbon (4.0 g) and acetic acid (10 ml) added and the reaction mixture was stirred under an atmosphere of hydrogen for 3 hours. Further fresh palladium on carbon (4.0 g) and acetic acid (20 ml) added and the reaction mixture was stirred under an atmosphere of hydrogen for a further 16 hours. The mixture was filtered through Celite, evaporated and the residue dissolved in ethyl acetate (300 ml) washed with water (2×100 ml), saturated sodium bicarbonate solution (2×100 ml) and brine (100 ml) and then passed through a hydrophobic frit and evaporated. The crude product was purified by column chromatography (silica) eluting with ethyl acetate (100% to 0%): methanol to give 2-{(3R,6R)-3-(2,3-dihydro-1H-inden-2-yl)-6-[(1S)-1-methylpropyl]-2,5-dioxo-1-piperazinyl}-N-(2-hydroxyphenyl)-2-(2-methyl-1,3-oxazol-4-yl)acetamide (11.8 g 51%)

HPLC Rt=3.2 minutes; m/z $[M+H]^+$=517.

Similarly prepared from (D)-isoleucine methyl ester hydrochloride

Intermediate 2

2-{(3R,6R)-3-(2,3-dihydro-1H-inden-2-yl)-6-[(1R)-1-methylpropyl]-2,5-dioxo-1-piperazinyl}-N-(2-hydroxyphenyl)-2-(2-methyl-1,3-oxazol-4-yl)acetamide HPLC Rt=3.17 and 3.22 minutes; m/z $[M+H]^+$=517.

Intermediate 3

{(3R,6R)-3-(2,3-dihydro-1H-inden-2-yl)-6-[(1S)-1-methylpropyl]-2,5-dioxo-1-piperazinyl}(2-methyl-1,3-oxazol-4-yl)acetic acid Carbonyldiimidazole (352 mg, 1.6 equiv.) was added to a solution of 2-{(3R,6R)-3-(2,3-dihydro-1H-inden-2-yl)-6-[(1S)-1-methylpropyl]-2,5-dioxo-1-piperazinyl}-N-(2-hydroxyphenyl)-2-(2-methyl-1,3-oxazol-4-yl)acetamide (11.8 g pre-dried in vacuo over $P_4O_{10}$ for 24 hours) in dichloromethane (20 mL) and the solution was left at room temperature for 16 hr. The mixture was evaporated and the residue dissolved in acetone (20 ml) and water (20 ml) added, followed by addition of 2NHCl (2 ml) and the mixture left at room temperature for 4.5 hr. This was extracted with ethylacetate (2×30 ml) and the combined organic phase dried via a hydrophobic frit and evaporated. The residue was taken up in ethylacetate (30 ml) washed with 2NHCl (2×10 ml) and then extracted with saturated sodium bicarbonate solution (2×15 ml). The combined aqueous phase was acidified with 2NHCl and extracted with ethylacetate (2×20 ml) and the combined organic phase washed with brine dried via a hydrophobic frit and evaporated to give {(3R,6R)-3-(2,3-dihydro-1H-inden-2-yl)-6-[(1S)-1-methylpropyl]-2,5-dioxo-1-piperazinyl}(2-methyl-1,3-oxazol-4-yl)acetic acid (0,355 mg, 73%) as a white solid.

HPLC Rt=3.0 and 3.1 minutes; m/z $[M+H]^+$=426
Similarly prepared from intermediate 2

{(3R,6R)-3-(2,3-dihydro-1H-inden-2-yl)-6-[(1R)-1-methylpropyl]-2,5-dioxo-1-piperazinyl}(2-methyl-1,3-oxazol-4-yl)acetic acid (Intermediate 4)

HPLC Rt=3.14 minutes; m/z $[M+H]^+$=426

Example 1

(3R,6R)-3-(2,3-dihydro-1H-inden-2-yl)-1-[(1R)-1-(2-methyl-1,3-oxazol-4-yl)-2-(4-morpholinyl)-2-oxoethyl]-6-[(1S)-1-methylpropyl]-2,5-piperazinedione m/z $[M+H]^+$=495
$^1$H NMR (CDCl$_3$) δ 7.72 (s, 1H), 7.26-7.15 (m, 4H), 6.93 (d, 1H), 6.30 (s, 1H), 4.18 (d, 1H), 4.06 (dd, 1H), 3.70-3.30 (m, 8H), 3.17-3.10 (m, 3H), 2.98-2.86 (m, 1H), 2.81-2.75 (m, 1H), 2.49 (s, 3H), 1.69-1.60 (m, 1H), 1.50-1.43 (m, 1H), 1.05-0.95 (m, 1H), 0.80-0.75 (m, 6H).

Similarly was prepared from intermediate 4 and morpholine

Example 2

(3R,6R)-3-(2,3-dihydro-1H-inden-2-yl)-1-[(1R)-1-(2-methyl-1,3-oxazol-4-yl)-2-(4-morpholinyl)-2-oxoethyl]-6-[(1R)-1-methylpropyl]-2,5-piperazinedione HPLC Rt=2.92 minutes; m/z $[M+H]^+$=495

Example 3

(3R,6R)-3-(2,3-dihydro-1H-inden-2-yl)-1-[(1R)-1-(2-methyl-1,3-oxazol-4-yl)-2-(4-morpholinyl)-2-oxoethyl]-6-[(1S)-1-methylpropyl]-2,5-piperazinedione (2R)-[(benzyloxycarbonyl)amino](2,3-dihydro-1H-inden-2-yl)ethanoic acid (35.84 g, 0.110 mol) in a 500 mL round bottomed flask was treated with 2,2,2-trifluoroethanol (165 mL) followed by methanol (55 ml) and triethylamine (11.13 g, 15.33 mL, 0.110 mmol) the slurry was stirred for 3.5 hrs until dissolution was observed. The solution was then added to (D)-allo Isoleucine methyl ester hydrochloride (20 g, 0.110 mol) in a separate flask. The slurry was stirred until dissolution was observed. 2-methyl-4-formyloxazole (12.24 g, 0.110 mmol) was then added followed by 2-benzyloxyphenylisocyanide (23.04 g, 0.110 mmol). The dark brown reaction mixture was then stirred at 20-25° C. for 24 hrs. The solution was then concentrated to a volume of ca. 130 mL by distillation at reduced pressure. The solution was the diluted with dichloromethane (200 mL) and washed with water (2×200 mL). The organic phase was then diluted with N-methyl pyrrolidinone (460 mL) was and the dichloromethane removed by stirring at 40° C. under vacuum for 2 hrs. Acetic acid 46 mL) was then added followed by palladium on carbon catalyst (69.0 g of 10% Pd wt, 57% water, Johnson Matthey type 87 L) and the mixture hydrogenated under balloon pressure of hydrogen with rapid stirring for 2 hrs. The reaction mixture was then filtered, washed through with ethyl acetate (960 mL) and washed with 3% w/v aq sodium chloride solution (960 mL). The biphasic mixture was filtered and the organic phase separated and washed with 3% w/v aq sodium chloride solution (2×960 mL). The organic solution was then diluted with ethyl acetate (200 mL) and concentrated by distillation at atmospheric pressure by distilling out 385 mL of solvent. The concentrated solution at 20-25° C. was treated with 1,1'-carbonyldiimidazole (21.46 g, 0.132 mol) and stirred at 20-25° C. for 1 hr then treated with water (290 mL) and stirred rapidly at 20-25° C. for 24 hr. The mixture was allowed to settle and the ethyl acetate layer separated and discarded. The aqueous phase was washed with ethyl acetate (290 mL) and the mixture allowed to settle and the aqueous phase was separated and acidified to pH 1-2 by the addition of concentrated hydrochloric acid (18 mL). The aqueous phase was then extracted into ethyl acetate (290 mL and then 145 mL). The combined ethyl acetate solution was then concentrated by distillation at atmospheric pressure to a volume of ca. 93 mL. This solution was then diluted with tetrahydrofuran (62 mL) and treated with triethylamine (11.02 g, 15.20 mL, 0.109 mol) and cooled to −78° C. The solution was then treated with trimethylacetyl chloride (4.81 g, 4.92 mL, 39.90 mmol) and stirred at −78° C. for 7 hr. The reaction mixture was then treated with a solution of morpholine (15.82 g, 15.83 mL, 0.181 mol) in tetrahydrofuran (23 mL) and stirred at −78° C. for 1 hr 20 mins before being allowed to warm to 20-25° C. The solution was then diluted with ethyl acetate (76 mL) and washed with saturated aqueous sodium bicarbonate solution (2×153 mL) followed by water (153 mL). The organic solution was then diluted with ethyl acetate (54 mL) and distilled down to a volume of 69 mL at atmospheric pressure. The solution was then cooled to 20-25° C. at which point crystallisation of the title compound occurred. The slurry of was then cooled further to 0° C. before the title compound was isolated by filtration and sucked dry. Yield 8.92 g.

Pharmacy Examples

These examples illustrate the preparation of a representative pharmaceutical formulations for administration containing a compound of the invention.

A. Parenteral Formulation

| Ingredients | |
|---|---|
| Compound of the invention | 1 g |
| Absolute alcohol | 5 mL |
| Propylene glycol | 25 mL |
| 5% w/v 2-hydroxypropyl β cyclodextrin in 50 mM acetic acid containing 0.9% sodium chloride adjusted to pH 4.0 with sodium hydroxide. | q.s. 100 mL |

The compound of the invention is dispersed in the alcohol and dissolved in the propylene glycol by the aid of heat. The aqueous component is then added with stirring to provide 10 mL of the I.V. solution.

The solution may be sterilised by appropriate means such as aseptic filtration or autoclaving.

This may be administered by bolus or diluted into an infusion bag containing, for example normal saline.

B. Capsule for Oral Administration.

| Ingredients | % wt./wt. |
|---|---|
| Compound of the invention | 25.0 |
| Lactose | 74.5 |
| Magnesium stearate | 0.5 |

The above ingredients are mixed and dispensed into hard gelatin capsules containing 100 mg each.

C. Tablet for Oral Administration.

| Ingredients | % wt./wt. |
|---|---|
| Compound of the invention | 25.0 |
| Lactose | 35.0 |
| Starch | 34.5 |
| Crospovidone | 4.0 |
| Magnesium stearate | 0.5 |

The above ingredients with the exception of the magnesium stearate are combined and mixed. The magnesium stearate is then added and the formulation mixed. The formulation is formed into tablets with an appropriate tableting machine.

Measurement of Oxytocin Antagonist Activity

Assay Buffer used throughout the assay: 50 mM HEPES, 10 mM MgCl2, 0.125 mg/ml BSA, pH adjusted to 7.4 with KOH.

hOT-CHO membranes were prepared at a concentration of 0.3 mg protein/ml in assay buffer. Test compounds were initially dissolved in DMSO (to 10 mM) and diluted in DMSO (Beckman Biomek FX). 1 µl of compound was transferred to black 384 assay plates (NUNC) using a Biomek FX. 20 µl of 1 nM Bodipy TMR Oxytocin (Perkin Elmer) in assay buffer was added to all wells (Labsystems Multidrop) then 20 µl membrane added to all wells (Multidrop). Plates were incubated at room temp for 60 min.

Polarisation was read on LJL Analyst (λEx=535 nm, λEm=580 nM, λDichroic=555 nm). Data were fitted to a 4 parameter logistic equation. An estimated Ki was calculated as IC50/5.

In the above test compounds of examples 1 and 2 of the invention have a pKi value of 9.0 and 8.2 respectively.

The compounds of the invention are essentially non toxic at therapeutically active doses. Thus compound of the example 1 has been administered to rats at doses of 30 mg/kg for 7 days and no adverse toxicological effects were observed.

The invention claimed is:

1. A method of treating a disease or condition mediated by oxytocin, wherein said method comprises administering (3R,6R)-3-(2,3-dihydro-1H-inden-2-yl)-1-[(1R)-1-(2-methyl-1,3-oxazol-4-yl)-2-(4-morpholinyl)-2-oxoethyl]-6-[(1S)-1-methylpropyl]-2,5-piperazinedione to a patient in need thereof wherein said disease or condition is endometriosis or dysmenorrhea.

2. The method of claim 1, wherein said (3R,6R)-3-(2,3-dihydro-1H-inden-2-yl)-1-[(1R)-1-(2-methyl-1,3-oxazol-4-yl)-2-(4-morpholinyl)-2-oxoethyl]-6-[(1S)-1-methylpropyl]-2,5-piperazinedione is administered parenterally.

3. The method of claim 1, wherein said (3R,6R)-3-(2,3-dihydro-1H-inden-2-yl)-1-[(1R)-1-(2-methyl-1,3-oxazol-4-yl)-2-(4-morpholinyl)-2-oxoethyl]-6-[(1S)-1-methylpropyl]-2,5-piperazinedione is administered orally.

4. The method of claim 1, wherein said (3R,6R)-3-(2,3-dihydro-1H-inden-2-yl)-1-[(1R)-1-(2-methyl-1,3-oxazol-4-yl)-2-(4-morpholinyl)-2-oxoethyl]-6-[(1S)-1-methylpropyl]-2,5-piperazinedione is administered as a dosage of 2-800 mg per day.

5. The method of claim 1, wherein said patient is a human patient.

6. A method of treating a disease or condition mediated by oxytocin, wherein said method comprises administering a pharmaceutical composition comprising (3R,6R)-3-(2,3-dihydro-1H-inden-2-yl)-1-[(1R)-1-(2-methyl-1,3-oxazol-4-yl)-2-(4-morpholinyl)-2-oxoethyl]-6-[(1S)-1-methylpropyl]-2,5-piperazinedione and at least one pharmaceutically acceptable carrier to a patient in need thereof.

7. The method of claim 1, wherein said disease or condition is endometriosis.

8. The method of claim 1, wherein said disease or condition is dysmenorrhea.

\* \* \* \* \*